US00PP32386P2

(12) United States Plant Patent
Palmer

(10) Patent No.: US PP32,386 P2
(45) Date of Patent: Oct. 20, 2020

(54) ***RUDBECKIA* PLANT NAMED 'RRICG02-0'**

(50) Latin Name: *Rudbeckia hirta*
Varietal Denomination: RRICG02-0

(71) Applicant: Garden Genetics, LLC, Bellefonte, PA (US)

(72) Inventor: Irene E. Palmer, Arden, NC (US)

(73) Assignee: Garden Genetics, LLC, Bellefonte, PA (US)

( * ) Notice: Subject to any disclaimer, the term of this patent is extended or adjusted under 35 U.S.C. 154(b) by 0 days.

(21) Appl. No.: 16/602,501

(22) Filed: Oct. 17, 2019

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Rudbeckia hirta* plant named 'RRICG02-0' is disclosed, characterized by strong, dense branching, and single inflorescences with dark gold ray florets and medium-dark red eyes. The new variety is a *Rudbeckia*, and is normally used as a garden or container plant.

2 Drawing Sheets

Figure 1:
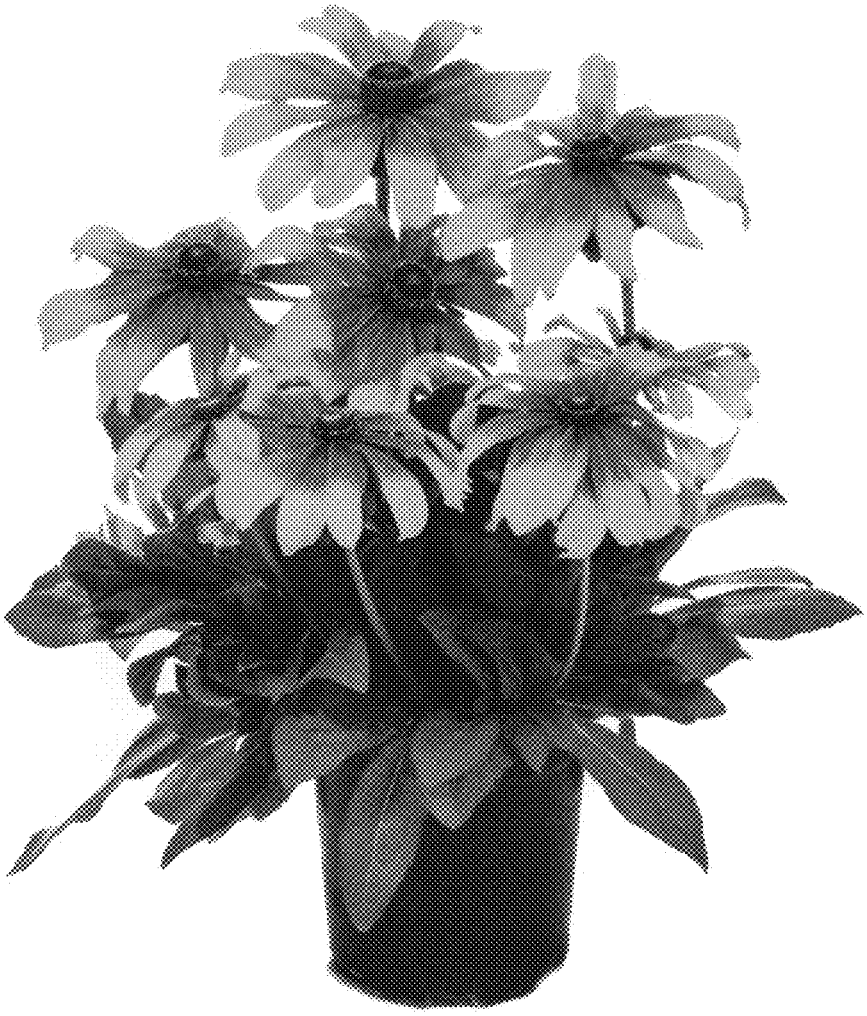

Latin name of the genus and species: *Rudbeckia hirta.*
Variety denomination: 'RRICG02-0'.

BACKGROUND OF THE INVENTION

The new cultivar is the product of a planned hybridization by the inventor. The crossing resulting in the new variety was made in October 2014 at a nursery in Bellefonte, Pa. The new variety was found and selected by the inventor in July 2015 at the same nursery in Bellefonte, Pa.

Asexual reproduction of the new cultivar 'RRICG02-0' by terminal vegetative cuttings was performed at the same nursery in Bellefonte, Pa. in August 2015. Subsequently, reproduction has also been successful by tissue culture. Vegetative reproduction by tissue culture has produced several generations, and has shown that the unique features of this cultivar are stable and reproduced true to type through successive generations.

SUMMARY OF THE INVENTION

The cultivar 'RRICG02-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RRICG02-0.' These characteristics in combination distinguish 'RRICG02-0' as a new and distinct *Rudbeckia hirta* cultivar:

1. Single inflorescences.
2. Dark gold ray florets, with a medium-dark red eye.
3. Ray florets are somewhat reflexed at full maturity.

4. Strong, dense branching.
5. 28-30" tall.

PARENT COMPARISON

Plants of the new cultivar 'RRICG02-0' are similar to plants of the seed parent variety, the unpatented *Rudbeckia* '1002-1', in most horticultural characteristics. However, plants of the new cultivar 'RRICG02-0' differ in the following ways:

1. Seed parent is dwarf and compact; new variety is tall in height.
2. Seed parent has small clear inflorescences; new variety has extremely-large dark gold inflorescences with a medium-dark red eye.
3. Seed parent has moderate branching; new variety is more densely branched.
4. Seed parent stops growing once the flowers senesce; new variety continues to grow and flower.

Plants of the new cultivar 'RRICG02-0' are similar to plants of the pollen parent variety, the unpatented *Rudbeckia* '7016-5', in most horticultural characteristics. However, plants of the new cultivar 'RRICG02-0' differ in the following ways:

1. Pollen parent has red-violet ray florets with a darker eye; new variety has dark gold_ray florets.
2. Pollen parent is intermediate in height, 18-24" tall; new variety is taller, 28-30" in height.
3. Pollen parent is large-flowered (5-6" in diameter); new variety is extremely large-flowered, with individual inflorescences on well-grown plants averaging 7" to 8" in diameter.

COMMERCIAL COMPARISON

'RRICG02-0' can be compared to the commercially known variety *Rudbeckia hirta* 'Balrudosh', U.S. Plant Pat.

No. 25,496. These plants are similar in most horticultural characteristics. However, plants of the new cultivar 'RRICG02-0' differ in the following ways:

1. 'Baldorush' has double-type inflorescences; 'RRICG02-0' has single inflorescences.
2. 'Baldorush' has streaked ray florets; 'RRICG02-0' has solid-colored ray florets with a distinct "eye"
3. 'Baldorush' typically has medium-green leaves; 'RRICG02-0' has dark-green leaves.
4. 'Baldorush' has a moderately vigorous, upright habit; 'RRICG02-0' is more vigorous, taller, and is more densely-branched.

'RRICG02-0' can also be compared to the commercially known variety *Rudbeckia hirta* 'RUDHT37', U.S. Plant Pat. No. 30,657. These plants are similar in most horticultural characteristics. However, plants of the new cultivar 'RRICG02-0' differ in the following ways:

1. 'RUDHT37' has a broad, upright habit; 'RRICG02-0' is more upright than broad in habit.
2. 'RUDHT37' has large single inflorescences about 5-6" in diameter; flowers of 'RRICG02-0' are typically larger, 7-8" in diameter.
3. 'RUDHT37' flowers are yellow-orange; 'RRICG02-0' flowers are a dark gold, with a medium-dark red blotch at the base of each ray floret, creating a distinct eye.

BRIEF DESCRIPTION OF THE PHOTOGRAPHS

The accompanying photograph in FIG. 1 illustrates in full color a typical plant of 'RRICG02-0' grown in a greenhouse in Santa Paula, Calif. The plant is approximately 6 months old in a 1 gallon pot.

Figure 2:
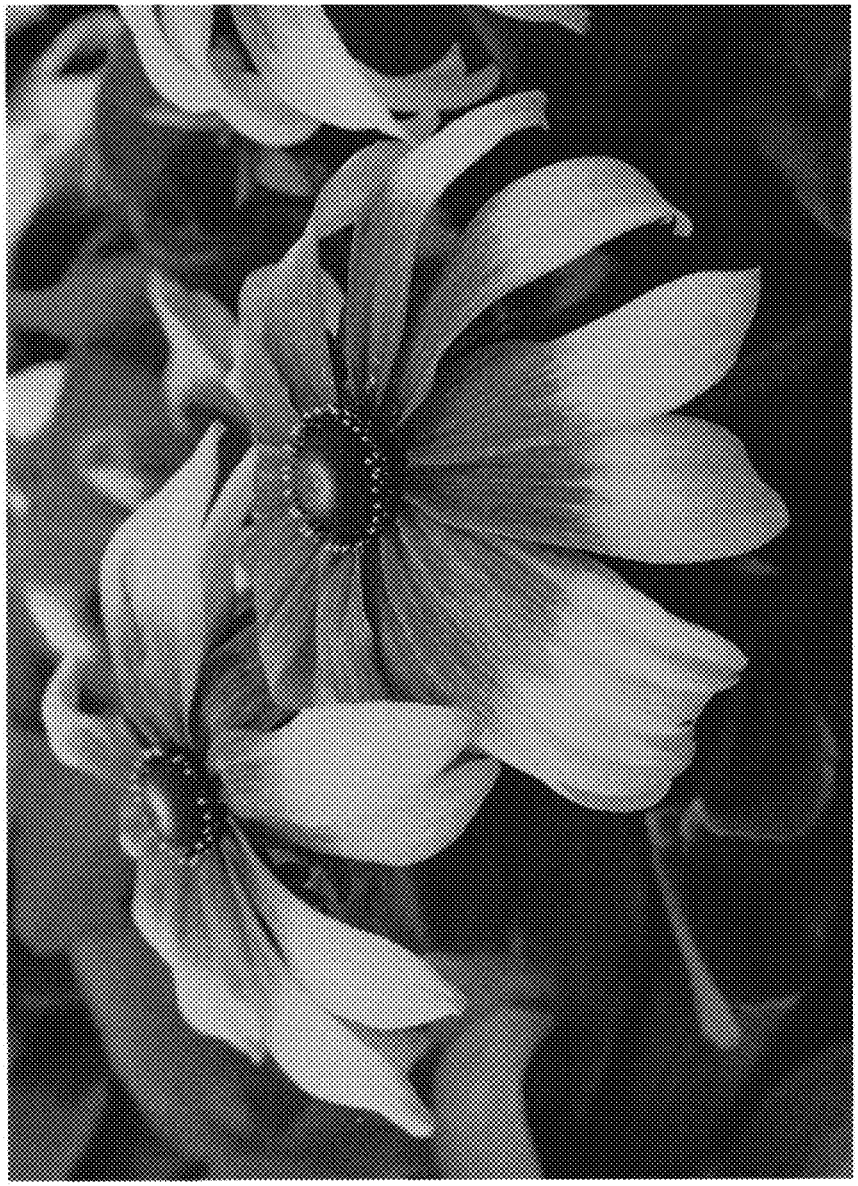

FIG. 2 illustrates a close-up view of typical inflorescence. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart 2007, except where general terms of ordinary dictionary significance are used. The following observations and measurements describe 'RRICG02-0' plants grown in a greenhouse during Winter and Spring in Santa Paula, Calif. The growing temperature ranged from 8° C. to 25° C. during the day and from 3° C. to 12° C. during the night. General light conditions are bright, normal sunlight. Measurements and numerical values represent averages of typical plant types. Plants are approximately 5 to 6 months old from a rooted cutting. No chemical or photoperiodic treatments were given.

Botanical classification: *Rudbeckia hirta* 'RRICG02-0'.

PROPAGATION

Time to initiate rooting: 7 to 10 days at approximately 25° C.

Time to produce a young rooted liner: Approximately 40 days at approximately 22° C.

Root description: Fine, well-branched, fibrous, becoming slightly woody with age.

PLANT

Growth habit: Hardy, upright, herbaceous perennial.

Height: To top of foliar plane: Approximately 50 cm. To top of flowering plane: Approximately 60 to 65 cm.

Plant spread: Approximately 50 cm.

Growth rate: Moderate.

Branching characteristics: Basal and low lateral branching. Well branched.

Length of branches: Approximately 22 to 35 cm, excluding peduncle.

Diameter branches: Approximately 5 to 7 mm.

Quantity of branches: Approximately 4 to 6 basal branches, each basal branch with 2 to 4 lateral branches.

Texture of lateral branches: Hispid. Hairs 3 to 4 mm long, colored near White 155A.

Color of lateral branches: Between RHS Green 143A and Green 137A. Internodes and region near internodes flushed Greyed-Purple N186C.

Aspect: Approximately 10° to 15° angle from base of plant.

Strength of lateral branches: Very strong.

Internode length: Average range 6.0 to 9.5 cm.

Age of plant described: Approximately 5 to 6 months old.

FOLIAGE

*Arrangement.*—Flowering stems produce sub-opposite or alternate occurring foliage. Basal foliage occurs in irregular whorls. Average Length: Average range 10 to 14.5 cm. Average Width: Average range 3.5 to 5.5 cm. Shape of blade: Elliptic. Apex: Acute. Base: Attenuate. Attachment: Sessile Margin: Sparsely serrate and densely ciliate. Texture of top surface: Densely pilose to nearly hirsute, hairs stiff, but, soft. Average hair length approximately 2 mm, colored near RHS White 155A. Texture of bottom surface: Densely pilose to nearly hirsute, hairs stiff, but, soft. Average hair length approximately 2 mm, colored near RHS White 155A.

*Color.*—Young foliage upper side: Near RHS Green 137A. Young foliage under side: Near RHS Green 138A. Mature foliage upper side: Near RHS Green 137A. Mature foliage under side: Near RHS Green 137B. Venation: Type: Pinnate Venation color upper side: Near RHS Yellow-Green 144B. Venation color under side: Near RHS Green 138B.

INFLORESCENCE

Bloom Period: Naturally blooming continuously from Spring to mid-Fall. During this time, blooming begins approximately 20 weeks after planting a rooted liner.

Bud:

*Bud shape.*—Globular.

*Bud length.*—Approximately 8 mm.

*Bud diameter.*—Approximately 9 mm.

*Bud color.*—Near Green 143A, streaked Yellow-Green 144C.

Inflorescence:

*Form.*—Terminal capitulum consisting of numerous disc florets, one or two rows of ray florets and two rows of involucral bracts.

*Diameter of entire inflorescence.*—Fully extended florets create an inflorescence diameter averaging 18 to 20 cm. With age, florets reflex downward, diameter of this fully mature inflorescence is 10 to 15 cm on average.

*Depth of inflorescence.*—Approximately 6.0 cm, with ray florets downwardly reflexed.

*Disc diameter.*—Approximately 2.7 to 3.1 cm.
*Receptacle shape.*—Conical.
*Receptacle height.*—Average 1.3 to 2.0 cm.
*Receptacle diameter.*—Average 1.5 cm at base, apex near 6 mm.
*Receptacle color.*—Near RHS White 155A.
*Quantity of inflorescences per lateral stem.*—1.
*Quantity of open inflorescence and buds per plant.*—Average 10 to 14 fully open inflorescences, and 10 to 14 buds.
*Longevity.*—Average 4 weeks on the plant without significant fading or aging. Persistent.
*Fragrance.*—Faint to moderate earthy scent.

Ray florets:
*Arrangement.*—Rotate, single to double row.
*Shape.*—Elliptic, or double elliptic.
*Number of ray florets.*—Average range 15 to 17.
*Length.*—Approximately 6.5 to 7.5 cm.
*Width.*—Approximately 2.2 to 2.4 cm.
*Apex shape.*—Round, or 2 irregular shallow lobes, with round apices.
*Base.*—Attenuate.
*Margin.*—Entire.
*Texture all surfaces.*—Smooth, matte, ribbed lengthwise.

Color:
Ray florets:
*Upper surface at first opening.*—Upper approximate 50% near RHS Yellow-Orange 17C, lower 50% Greyed-Orange 175B streaked 17C. Apex flushed Yellow-Green 144A.
*Upper surface at maturity.*—Upper approximate 50% near RHS Yellow-Orange 17B, lower 50% a color between Orange-Red N34A and Greyed-Purple 183A lightly streaked 17C.
*Under surface at first opening.*—Near RHS Yellow 2B, streaked near Green 143A.
*Under surface at maturity.*—Upper 50% near RHS Yellow 13B, veins faintly Green 143B. Lower 50% near Yellow 13B flushed Brown 200B, very faint veins Green 143A.

Disc florets:
*Number of disc florets.*—Approximately 400.
*Arrangement.*—Acropetally on disc.
*Length.*—Approximately 4 to 7 mm.
*Width.*—Approximately 1 mm.
*Shape.*—Tubular.
*Margin.*—Entire.
*Apex.*—Rounded when immature, serrate with age.
*Base.*—Fused.
*Texture.*—Matte. Color Disc Florets: At first opening: Near RHS Brown 200A, base near White 155D. At maturity: Near RHS Brown 200A, base near White 155D. Fading: Near RHS Brown 200A.

Phyllaries/involucral bracts:
*Arrangement.*—Rotate, in 2 or 3 rows.
*Number.*—Approximately 25.
*Length.*—Average range 14 to 19 mm.
*Width.*—Approximately 3 to 6 mm.
*Shape.*—Lanceolate. Apex: Acute. Base: Truncate, fused. Margin: Entire, ciliate. Texture: Sericeous upper and lower surfaces. Color: Inside color near RHS Green 137A. Outside color near RHS Green 138A.

Peduncle:
*Length.*—Average range 10 to 18 cm.
*Width.*—Average 5 mm.
*Texture.*—Hispid.
*Color.*—Near RHS Green 143A.
*Strength.*—Very strong.

REPRODUCTIVE ORGANS

Ray florets:
Gynoecium: Rarely present, less than 10 to 20% of florets. Malformed.
*Pistil length.*—Approximately 4 mm.
*Stigma shape.*—Linear.
*Stigma color.*—Near RHS White 155D.
*Style length.*—About 2 mm.
*Style color.*—Near White 155D.
*Ovary color.*—Detected in less than 5% of florets. Near RHS Green 143B.
Androecium: Not present.

Disc florets:
Androecium:
*Stamen number.*—2 to 4. Filament length: Average 3 mm. Filament color: Near Greyed-Purple N186C. Anther shape: Forked/curled. Anther length: 0.5 mm. Anther color: RHS Greyed-Purple N186C. Pollen amount: Abundant. Pollen color: Near RHS Yellow-Orange 15A.
Gynoecium:
*Pistil length.*—Approximately 4 mm.
*Stigma shape.*—Decurrent.
*Stigma color.*—Near RHS Greyed-Purple N186C.
*Style length.*—About 3 mm.
*Style color.*—Lower section near RHS White 155C, upper section near Greyed-Purple N186C.
*Ovary color.*—Near RHS White 155C.

OTHER CHARACTERISTICS

Disease resistance: Neither resistance nor susceptibility to diseases or pests normal to *Rudbeckia* have been observed in this variety.

Drought tolerance and temperature tolerance: Hardy perennial, low temperature tolerance to USDA Zone 4, at least. Tolerates high temperature extremely well, to at least 35° C. Some drought tolerance. Plants can be allowed in dry soil for several days without damage.

Fruit/seed production: Low seed production. Oblong achene, approximately 3 mm long, 1 mm wide, colored near RHS Brown 200A.

What is claimed is:

1. A new and distinct cultivar of *Rudbeckia* plant named 'RRICG02-0' as herein illustrated and described.

* * * * *